United States Patent
Bertho et al.

[11] Patent Number: 6,156,543
[45] Date of Patent: *Dec. 5, 2000

[54] METHOD FOR PREPARING SURFACE-ACTIVE AGENTS

[75] Inventors: Jean-Noël Bertho, Pomacle; Philippe Mathaly; Véronique Dubois, both of Reims; Régis de Baynast de Septfontaines, Versailles, all of France

[73] Assignee: Agro Industrie Recherches et Developpements (A.R.D.), Pomacle, France

[*] Notice: This patent is subject to a terminal disclaimer.

[21] Appl. No.: 09/117,964
[22] PCT Filed: Feb. 7, 1997
[86] PCT No.: PCT/FR97/00249
§ 371 Date: Aug. 7, 1998
§ 102(e) Date: Aug. 7, 1998
[87] PCT Pub. No.: WO97/29115
PCT Pub. Date: Aug. 14, 1997

[30] Foreign Application Priority Data

Feb. 8, 1996 [FR] France .................. 96 01542

[51] Int. Cl.⁷ ..................................... C12P 19/44
[52] U.S. Cl. ............... 435/74; 435/96; 435/98; 435/99; 435/274; 435/276; 536/4.1; 536/6.3; 536/18.6
[58] Field of Search .................. 435/274, 276, 435/99, 96, 98, 74; 536/18.6, 4.1, 6.3

[56] References Cited

U.S. PATENT DOCUMENTS

| | | |
|---|---|---|
| 4,070,232 | 1/1978 | Funk . |
| 4,223,129 | 9/1980 | Roth et al. . |
| 4,338,399 | 7/1982 | Weil et al. ........................ 435/99 |
| 4,478,854 | 10/1984 | Adler-Nissen et al. ............ 426/12 |
| 5,688,930 | 11/1997 | Bertho et al. ...................... 536/18.6 |

FOREIGN PATENT DOCUMENTS

| | | |
|---|---|---|
| 2 580 669 A1 | 4/1985 | France . |
| 583137 | 1/1978 | U.S.S.R. . |
| WO 92/07098 | 4/1992 | WIPO . |

*Primary Examiner*—Francisco Prats
*Attorney, Agent, or Firm*—Knobbe, Martens, Olson & Bear, LLP

[57] ABSTRACT

Process for preparing surfactant, which comprises contacting cane trash, maize by-products, sorghum by-products, barley by-products, rice by-products, fruits, chicory pulp, tubers or cynara for at least 5 seconds with a hydrolysing agent selected from an aqueous acid solution at between 20 and 150° C. and an enzymatic hydrolysing composition of a plant material at between 20 and 90° C. to obtain a sugar syrup, freeing the sugar syrup from any solid residues and contacting the residue-free sugar syrup with a $C_{4-22}$-alcohol at a temperature of between 20 and 150° C., preferably between 30 and 110° C., until a solution of surfactant glycosides is obtained, and separating the surfactant glycosides from this solution.

25 Claims, 3 Drawing Sheets

METHOD FOR PREPARING SURFACE-ACTIVE AGENTS

This is the U.S. national phase under 35 U.S.C. § 371 of International Application PCT/FR97/00249, filed Feb. 7, 1997.

Process for preparing surfactant from cane trash, maize by-products, sorghum by-products, barley by-products, rice by-products, fruits, chicory pulp, tubers and Cynara.

The present invention relates to processes for preparing mixtures of alkyl glycosides which can be used as surfactants.

Grafting alkyl groups onto glucids produces surfactant agents with very valuable surface properties and generally with good biodegradability (R. D. Swisher, "Surfactant biodegradation", Marcel Dekker, Inc. NEW YORK, 1987).

The reaction which is most commonly found consists in glycosylating fatty alcohols with reducing sugars or intermediate glycosides. This is carried out in the presence of an acid catalyst and the alkyl glycosides obtained are stable over a wide pH range, notably neutral and basic. The substrate most often used as reducing sugar is glucose. The glycosylation carried out starting with this sugar results in mixtures of alkyl glycosides and polyglucosides which are known for their surfactant properties. These will have numerous applications from now on in fields as varied as detergents, the chemical and parachemical industries or in the medical field and in biology (cf. for example WO 93 07160, WO 93 07249, DE 42 12 080 Al, U.S. Pat. No. 4,987,225).

In order to prepare these alkyl glucosides it is necessary to have large quantities of glucose. Obtaining this glucose from cornflour, for example, requires numerous steps. In fact, it is essential to eliminate the proteins and purify the glucose notably by the steps of filtration and chromatography on ion exchanger resins.

The major drawback of this approach is the high cost of the raw material, which is especially due to the use of a refined agricultural substance such as flour and the numerous steps for purifying the glucose. All this naturally limits the potential applications of these processes. Moreover, the reaction of glycosylation of the glucose or other hexoses is carried out at high temperature (100 to 150° C.), causing the products to change colour.

American Patent 4,070,232 describes a process which comprises pre-hydrolysing vascular plants in an acid medium with heating and separating a liquid phase containing pentoses and hexoses from a fibrous phase. The sugars have to be purified before being used, optionally as sweeteners, substrates for animal feeds, wetting agents, surfactants, polyols, sequestering agents and emulsifiers.

The invention relates to a process for preparing surfactant agents, characterised in that it comprises contacting cane trash, maize by-products, sorghum by-products, barley by-products, rice by-products, fruits, chicory pulp, tubers or Cynara for at least 5 seconds with a hydrolysing agent selected from an aqueous acid solution at between 20 and 150° C. and an enzymatic hydrolysing composition of a plant material at between 20 and 90° C. to obtain a sugar syrup, if necessary, freeing the sugar syrup from any solid residues and contacting the residue-free sugar syrup with a $C_{4-22}$-alcohol at a temperature of between 20 and 150° C., preferably between 30 and 110° C., until a solution of surfactant glycosides is obtained, and separating the surfactant glycosides from this solution.

This process has the advantage of using sugars which are currently hardly used such as pentoses and uronic acids which are obtained, respectively, from the hydrolysis of hemicellulose and pectin, and of working with mixtures of these sugars as starting materials and consequently avoiding the steps of purification such as crystallisation. Moreover, we were surprised to find that the oligomers are grafted with a fatty alcohol which makes it possible, in particular, to improve the grafting yields and make full use of the sugar-containing liquor, unlike U.S. Pat. No. 4,070,232.

The syrup consists notably of pentoses, particularly D-xylose and L-arabinose and sometimes uronic acids such as D-galacturonic acid. Surprisingly, we found that the pentoses such as D-xylose and L-arabinose and D-galacturonic acid had the advantage of being more reactive during glycosylation. This property allows grafting under controlled conditions which, in particular, avoid any degradation of the reagents or reaction products. In contrast to the preparation of alkyl glucosides and polyglucosides, which requires temperatures generally above 120° C. (cf. DE 42 12 080, WO 93 07160), the alkyl glycosides according to the present invention may be synthesised at a temperature below 100° C. Moreover, at the same temperature, we demonstrated that the glycosidation of arabinose, xylose and galacturonic acid takes place more rapidly than the glycosidation of glucose. At 80° C., starting from crystallised sugars, under the same reaction conditions and after 1 hour's reaction, 100% of the D-galacturonic acid and 87% of the L-arabinose have been used up, whereas 97% of residual D-glucose still remains.

Moreover, we were able to demonstrate, by working with D-glucose and L-arabinose this time, that there was a synergy between these two sugars. In fact, D-glucose reacts more rapidly in the presence of arabinose than it does on its own in the reaction mixture. At 80° C., starting from crystallised sugars, under the same reaction conditions and after 2 hours' reaction, 25% and 40% of the starting D-glucose remain, when it is treated in admixture with 90% and 40% of L-arabinose, respectively, whereas 60% of the starting D-glucose remain when it is used in pure form. These results confirm our approach which consists in starting with a mixture of sugars containing pentoses. The reaction times are thus considerably reduced.

According to the present invention, the yields of surfactants from cane trash, maize by-products, sorghum by-products, barley by-products, rice by-products, fruits, chicory pulp, tubers and Cynara are similar to those which are theoretically obtained from these plants, taking account of the composition of hemicellulose and pectins in the raw material. Thus, in coarse maize bran, for a theoretical composition of 55% of glycosidable sugars, in relation to the total dry matter, we graft 49% of the starting dry matter after purification, i.e. 90% of the potential.

There is also the possibility of separately obtaining surfactants derived from non-charged neutral sugars (pentoses and hexoses) and surfactants derived from anionic sugars (galacturonic acid).

Moreover, the reaction of glycosylation may be carried out without the addition of supplementary acid catalysts; the acidity of the syrup is sufficient to catalyse the reaction.

The invention sets out to obtain surfactants from a particularly cheap raw material by operating steps which are simple and few and which do not require the use of high temperatures causing colour changes.

According to the invention, cane trash, maize by-products, sorghum by-products, barley by-products, rice by-products, fruits, chicory pulp, tubers and Cynara are used as raw materials for the preparation of surfactants.

By maize and sorghum by-products is meant the entire plant and/or its constituent parts (cobs, shucks, stems and leaves) which can be harvested directly or obtained from the waste after separation of the grains.

It is also possible to use maize or rice fibre. Maize fibre means the compounds obtained during a process of fractionation intended in particular for the production of starch.

The bran is obtained after grinding in a seed mill. It is made up of hemicellulose consisting of polymers of xylose and arabinose, and cellulose. It is also possible to use barley fibres obtained from breweries. These fibres correspond to the residues obtained after pressing the sweetened barley malt.

According to the invention, the term fruit chiefly refers to so-called complex fruits such as apples or fleshy fruits such as cedrate fruits.

It is also possible to use the by-products of the fruit juice industry such as apple, pear or citrus residues.

These different residues are made up of hemicelluloses consisting of arabinose and galactose monomers and pectins consisting essentially of galacturonic acid monomers.

According to the invention, tubers such as potatoes or onions can be used.

It is also possible to use onion or potato peelings as well as primary transformation products such as mashed potato and chips. Potato or onion peelings are made up of hemicelluloses consisting of arabinose and xylose monomers and pectins consisting of galacturonic acid monomers.

According to the invention, Cynara is also used: the term Cynara denotes any plant belonging to the Cynara family such as artichokes (Cynara scolymus) or any hybrid plant produced by crossing a Cynara and a Carduus or a Cirsium (cardoon).

Where the starting substrate does not contain any pectins (FIG. 1), the first step of the process according to the invention consists in contacting cane trash, maize by-products, sorghum by-products, barley by-products and rice by-products with an aqueous acid solution (2). Thus, the hemicellulose of the cane trash, maize by-products, sorghum by-products, barley by-products and rice by-products (1) is extracted, solubilised and hydrolysed in an aqueous medium in the presence of acid or enzymes. The acid used may be hydrochloric acid, hydrobromic acid, sulphuric acid, phosphoric acid, a sulphonic acid such as benzene sulphonic acid, p.toluenesulphonic acid, camphor sulphonic acid, sulphosuccinic acid or an alkyl sulphosuccinate such as decyl or lauryl sulphosuccinate, perhalohydric acids such as perchloric acid, for example.

Figure 1:
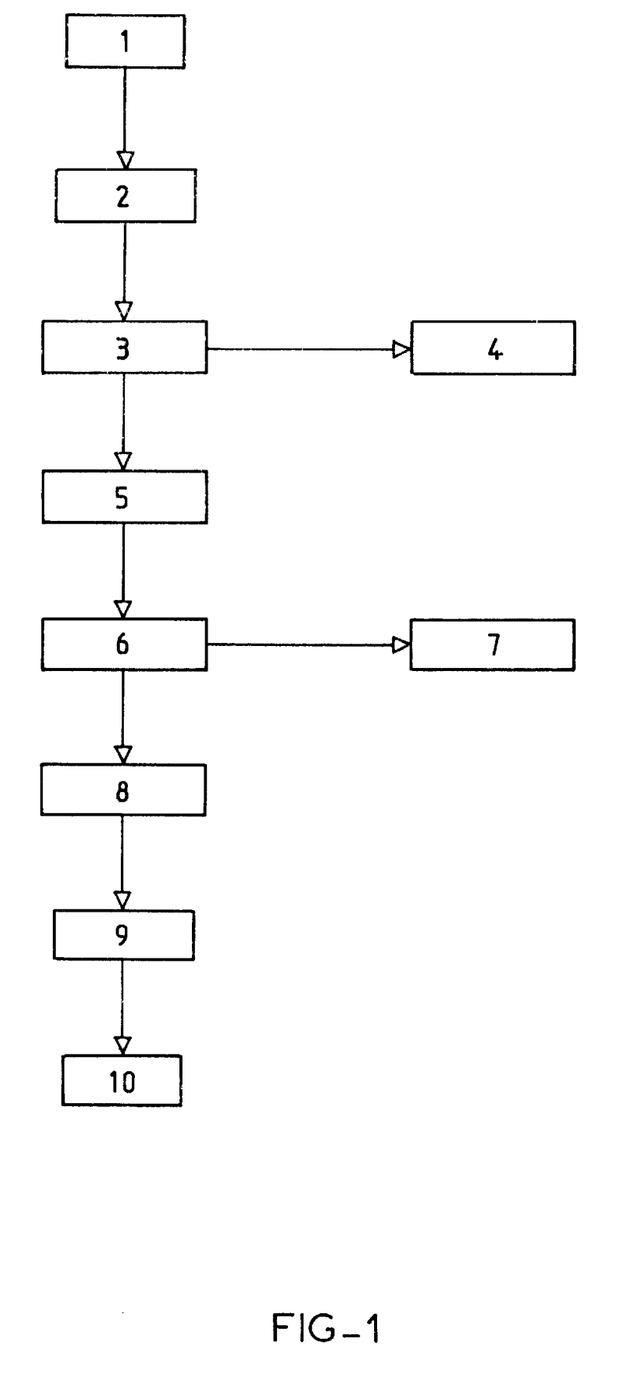
FIG. 1 shows a block diagram of the steps in a process according to an embodiment of the invention where the starting substrate does not contain any pectins.

Addition to an acid medium is generally carried out for 5 to 90 minutes in a simple mixer. However, the contact time can be reduced to a few seconds if an apparatus is used which allows mixing to be carried out on a production line, known as a "jet cooker". The first step may also be carried out by enzymatic hydrolysis. The enzymes used may be a multienzyme complex containing hemicellulases, cellulases, β-glucanases, proteases and esterases. The enzymatic hydrolysis is carried out in an aqueous medium for at least one hour at a temperature of between 20 and 90° C.

The second step of the process according to the invention (3) comprises freeing the sugar syrup from a solid residue (4). This operation is advantageously carried out by pressing under a pressure of the order of $1.10^5$ to $500.10^5$ Pascals, preferably of the order of $5.10^5$ to $60.10^5$ Pascals using a screw press, filter press or any other equipment for squeezing a liquor from a wet residue. In this way a sugar-containing liquor is obtained (5).

The sugar liquors may optionally be changed into acid form by ion exchange on a cation exchanger resin or by electrodialysis (9).

The sugar syrup can also be concentrated by evaporation down to 30 to 95% and more particularly 60 to 80% of dry matter (9). The sugar syrup, freed from solid residue, has a sugar purity generally between 50 and 95%, based on dry matter.

The third step of the process according to the invention consists in contacting the sugar syrup, freed from residue, with a $C_{4-22}$-alcohol. The alcohol corresponds to the formula $R^1OH$, where $R^1$ is a straight-chained or branched $C_{6-22}$-alkyl radical, a hydrocarbon radical having 1 to 4 ethylenically unsaturated bonds and 4 to 22 carbon atoms or one of these radicals substituted with 1 to 3 substituents on different carbon atoms selected from among hydroxy, halogen and trifluoromethyl. Fatty alcohols having 8 to 16 carbon atoms are particularly preferred, notably mixtures of octanol and decanol, mixtures of decanol and dodecanol, mixtures of dodecanol and tetradecanol and mixtures of dodecanol, tetradecanol and hexadecanol. Generally, 1 to 4 equivalents of alcohol are used in relation to the sugars. However, it is preferable during a first stage to carry out the glycosylation of a short alcohol with sugar syrups. Then transglycosylation with fatty alcohols of formula $R^1OH$ is carried out. The short alcohol corresponds to formula $R^2OH$, where $R^2$ is a straight-chained alkyl radical having 1 to 5 carbon atoms. It is preferred to carry out this reaction of glycosylation in the total absence of solvents but if necessary a solvent such as an ether oxide may be used, e.g. tetrahydrofuran, diethyl oxide, 1,4-dioxane, isopropyl oxide, methyl-tert.-butyl ether, ethyl-tert.-butyl ether or diglyme, a halohydrocarbon such as methylene chloride, chloroform, 1,2-dichloroethane, a nitro solvent such as nitromethane, nitro-2-propane, a solvent from the amide family such as N-methylformamide, N,N-dimethylformamide, N,N-dimethylacetamide, N-methyl-2-pyrrolidone, a nitrile such as acetonitrile, an alkane such as hexane, heptane or octane, or an aromatic solvent such as toluene or xylene. It is preferable to carry out this reaction at between 30 and 110° C. in order to prevent the formation of coloured product as far as possible, but it is possible to carry out the reaction at temperatures up to 150° C. If the sugar liquor has been completely demineralised, 0.1 to 5% by mass, based on the dry matter of the syrup, of an acid catalyst must be added to the reaction medium. This acid may be hydrochloric acid, sulphuric acid, phosphoric acid, a sulphonic acid such as benzenesulphonic acid, p.toluenesulphonic acid, camphorsulphonic acid, sulphosuccinic acid or an alkyl sulphosuccinate such as decyl or lauryl sulphosuccinate, the perhalohydric acids such as perchloric acid, for example. This acid catalysis may also be carried out with 0.05 to 6 equivalents by weight of a sulphone resin in its $H^+$ form, or an acid resin. It is preferable to avoid total demineralisation of the pressed liquor and consequently the addition of acid catalysis.

In order to collect the mixture of alkyl glycosides, the process consists of:

eliminating the reaction solvent, if there is one, neutralising the acidity of the starting syrup or the acid catalyst, then optionally filtering the salt obtained. The neutralisation is carried out, for example, with an alkali metal or alkaline earth metal carbonate or hydrogen carbonate, particularly sodium hydrogen carbonate, with an alkali or alkaline earth metal hydroxide, particularly sodium hydroxide. A surfactant is then obtained in accordance with the invention in the form of a self-emulsifying base.

However, if desired, the product may be purified:

either by evaporation of the excess fatty alcohol in a vacuum between 0.001 and 10 mbar at a temperature between 60 and 250° C., or by chromatography on a column of silica gel, aluminium oxide, activated charcoal or on an ion exchanger resin, or by crystallisation from a solvent or mixture of suitable solvents selected from the ether oxides such as tetrahydrofuran, diethyl oxide, 1,4-dioxane, isopropyl oxide, methyl-tert.-butyl ether, ethyl-tert.-butyl ether or diglyme, a halohydrocarbon such as methylene chloride, chloroform, 1,2-dichloroethane, a nitro solvent such as nitromethane, nitro-2-propane, a solvent from the amide family such as N-methylformamide, N,N-dimethylformamide, N,N-dimethylacetamide, N-methyl-2-pyrrolidone, a nitrile such as acetonitrile, an alkane such as hexane, heptane or octane or an aromatic solvent such as toluene or xylene, or by selective extraction with water-immiscible solvents. The isolated product then has a percentage of residual fatty alcohol of between 0 and 5%, preferably between 0 and 1%.

Optionally solubilising the surfactant in water to obtain a surfactant composition having a content of dry matter of 20 to 80%, if necessary, decolorising this solution by adding, at a temperature between 15 and 100° C., 0.05 to 10% and preferably 0.5 to 3% of hydrogen peroxide, alkali metal or alkaline earth metal peroxodisulphates, perborates, persulphates, perphosphates, percarbonates, ozone or periodinates. 30 or 50% hydrogen peroxide is preferred. The decolorising agent according to the invention should of course be compatible with all the ingredients of the final formulation and with the uses of the finished products.

If the starting substrate contains pectins (FIGS. 2 and 3) the first step of the process according to the invention consists in bringing the fruits, the chicory pulp, tubers or Cynara (21, 31) in contact with an aqueous acid solution (22, 32). Thus, the hemicellulose from the fruits, chicory pulp, tubers or Cynara is extracted, solubilised and hydrolysed in an aqueous medium in the presence of acid. During this treatment, the pectins of the fruits, chicory pulp, tubers or Cynara are solubilised (22, 32). The acid used may be hydrochloric acid, hydrobromic acid, sulphuric acid, phosphoric acid, a sulphonic acid such as benzenesulphonic acid, p.toluenesulphonic acid, camphor sulphonic acid, sulphosuccinic acid or an alkyl sulphosuccinate such as decyl or lauryl sulphosuccinate, the perhalohydric acids such as perchloric acid, for example.

Figure 2:
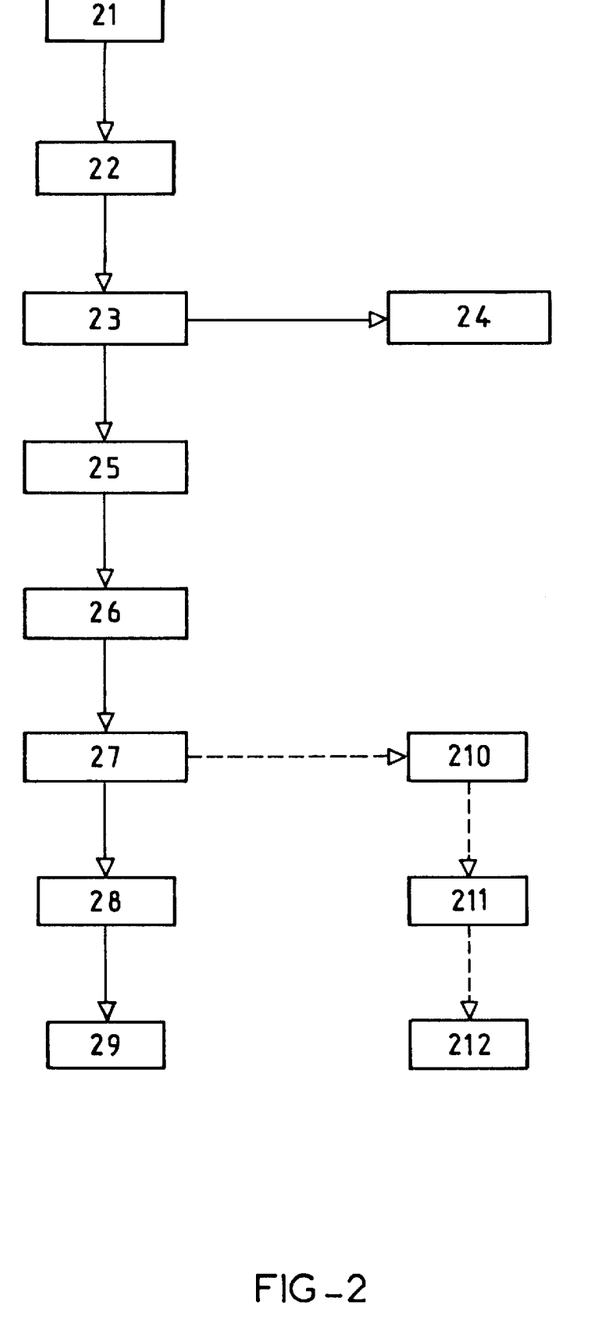
FIG. 2 shows a block diagram of the steps in a process according to an embodiment of the invention where the starting substrate contains pectins and where the hydrolysis is performed with enzymes.
Figure 3:
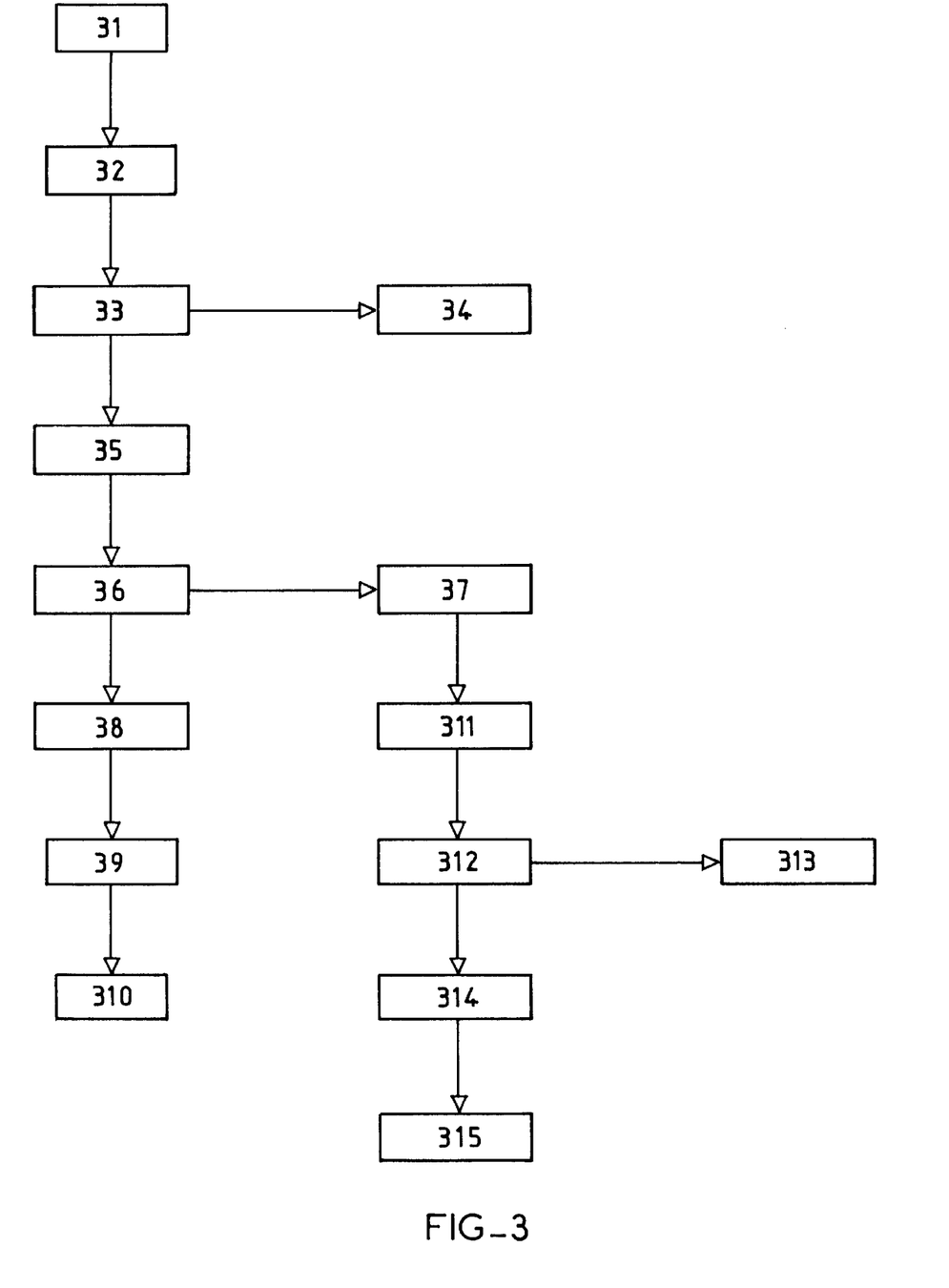
FIG. 3 shows a block diagram of the steps in a process according to an embodiment of the invention where the starting substrate contains pectins and where the hydrolysis is performed with an aqueous acid solution.

Generally, this contacting is carried out for 5 to 90 minutes in a simple mixer. However, the contact time can be reduced to a few seconds by using an apparatus for carrying out mixtures in series, known as a "jet cooker".

Thus, the first step may be carried out by enzymatic hydrolysis. The enzymes used may be a multi-enzyme complex which may contain hemicellulases, cellulases, β-glucanases, proteases, esterases and pectinases. The enzymatic hydrolysis is carried out in an aqueous medium for at least one hour at a temperature between 20 and 90° C.

The second step of the process according to the invention (23, 33) consists in freeing the sugar syrup of any solid residue (24, 34). This operation is advantageously carried out by pressing at a pressure of the order of $1.10^5$ to $500.10^5$ Pascals, preferably of the order of $5.10^5$ to $60.10^5$ Pascals using a screw press, filter presses, decanters or any other equipment for squeezing a liquor from the wet residue. In this way a sugar liquor is obtained (25, 35).

Complementary hydrolysis of the purified liquor (27) may optionally be carried out in order to obtain an enzymatically hydrolysed sugar liquor. This operation consists in contacting the liquor obtained from purification (26) with pectinases for at least 5 minutes at a temperature of between 10 and 60° C. at a pH of between 3 and 6 (27).

The hydrolysate obtained may also be converted into acid form by passing over a cation exchange resin or by electrodialysis (28).

The sugar syrup can also be concentrated by evaporation down to 30 to 95% and more particularly 60 to 80% of dry matter (29). The sugar syrup freed from solid residue has a sugar purity generally between 50 and 95% in relation to the dry matter.

The third step of the process according to the invention comprises contacting the sugar syrup free from residue with an alcohol having 4 to 22 carbon atoms using the method described for the treatment of raw materials containing no pectins.

For collecting the mixture of alkyl glycosides the process comprises:

eliminating the reaction solvent, if there is one, neutralising the acidity of the starting syrup or the acid catalyst, then optionally filtering the salt obtained. The neutralisation is carried out, for example, with an alkali metal or alkaline earth metal carbonate or hydrogen carbonate, particularly sodium hydrogen carbonate, with an alkali or alkaline earth metal hydroxide, particularly sodium hydroxide.

Optionally saponifying the alkyl (alkyl-D-galactoside) uronates formed during the grafting. For this operation an alkali or alkaline earth metal hydroxide may be used, particularly sodium hydroxide.

And if desired, the product may be purified:

either by evaporation of the excess fatty alcohol in a vacuum between 0.001 and 10 mbar at a temperature between 60 and 250° C., or by chromatography on a column of silica gel, aluminium oxide, activated charcoal or on an ion exchanger resin, or by crystallisation from a solvent or mixture of suitable solvents selected from the ether oxides such as tetrahydrofuran, diethyl oxide, 1,4-dioxane, isopropyl oxide, methyl-tert.-butyl ether, ethyl-tert.-butyl ether or diglyme, a halohydrocarbon such as methylene chloride, chloroform, 1,2-dichloroethane, a nitro solvent such as nitromethane, nitro-2-propane, a solvent from the amide family such as N-methylformamide, N,N-dimethylformamide, N,N-dimethylacetamide, N-methyl-2-pyrrolidone, a nitrile such as acetonitrile, an alkane such as hexane, heptane or octane or an aromatic solvent such as toluene or xylene, or by selective extraction with water-immiscible solvents. The isolated product then has a percentage of residual fatty alcohol of between 0 and 5%, preferably between 0 and 1%.

Optionally solubilising the surfactant in water to obtain a surfactant composition having a content of dry matter of 20 to 80%, if necessary, decolorising this solution by adding, at a temperature between 15 and 100° C., 0.05 to 10% and preferably 0.5 to 3% of hydrogen peroxide, alkali metal or alkaline earth metal peroxodisulphates, perborates, persulphates, perphosphates, percarbonates, ozone or periodinates. 30 or 50% hydrogen peroxide is preferred. The decolorising agent according to the invention should of course be compatible with all the ingredients of the final formulation and with the uses of the finished products.

If the starting substrate contains pectins a first variant of the process comprises after carrying out the complementary enzymatic hydrolysis which produces an enzymatically hydrolysed sugar liquor (FIG. 2 (22)), separating it into a liquor of neutral sugars and into a liquor of anionic sugars. This operation (27) can be carried out by electrodialysis or by fixing and then eluting the anionic sugars on an anionic ion exchange resin.

It is also possible to change the anionic sugar liquor obtained into acid form by passing it over a cation exchange resin or by electrodialysis (211).

The syrup of anionic sugars can also be concentrated by evaporation down to 30 to 95% and more particularly 60 to 80% of dry matter (212). The syrup of anionic sugars freed from solid residue has a degree of purity of anionic sugars which is generally between 50 and 95% based on the dry matter.

The third step of the process according to the invention comprises contacting the anionic sugar syrup freed from residue with a $C_{4-22}$-alcohol according to the procedure described for the treatment of raw materials containing no pectins.

For collecting the mixture of alkyl glycosides the process comprises:

eliminating the reaction solvent, if there is one, neutralising the acidity of the starting syrup or the acid catalyst, then optionally filtering the salt obtained. The neutralisation is carried out, for example, with an alkali metal or alkaline earth metal carbonate or hydrogen carbonate, particularly sodium hydrogen carbonate, with an alkali or alkaline earth metal hydroxide, particularly sodium hydroxide.

Optionally saponifying the alkyl (alkyl-D-galactoside) uronates formed during the grafting. For this operation an alkali or alkaline earth metal hydroxide may be used, particularly sodium hydroxide.

And if desired, the product may be purified:

either by evaporation of the excess fatty alcohol in a vacuum between 0.001 and 10 mbar at a temperature between 60 and 250° C., or by chromatography on a column of silica gel, aluminium oxide, activated charcoal or on an ion exchanger resin, or by crystallisation from a solvent or mixture of suitable solvents selected from the ether oxides such as tetrahydrofuran, diethyl oxide, 1,4-dioxane, isopropyl oxide, methyl-tert.-butyl ether, ethyl-tert.-butyl ether or diglyme, a halohydrocarbon such as methylene chloride, chloroform, 1,2-dichloroethane, a nitro solvent such as nitromethane, nitro-2-propane, a solvent from the amide family such as N-methylformamide, N,N-dimethylformamide, N,N-dimethylacetamide, N-methyl-2-pyrrolidone, a nitrile such as acetonitrile, an alkane such as hexane, heptane or octane or an aromatic solvent such as toluene or xylene, or by selective extraction with water-immiscible solvents. The isolated product then has a percentage of residual fatty alcohol of between 0 and 5%, preferably between 0 and 1%.

Optionally solubilising the surfactant in water to obtain a surfactant composition having a content of dry matter of 20 to 80%, if necessary, decolorising this solution by adding, at a temperature between 15 and 100° C., 0.05 to 10% and preferably 0.5 to 3% of hydrogen peroxide, alkali metal or alkaline earth metal peroxodisulphates, perborates, persulphates, perphosphates, percarbonates, ozone or periodinates. 30 or 50% hydrogen peroxide is preferred. The decolorising agent according to the invention should of course be compatible with all the ingredients of the final formulation and with the uses of the finished products.

It is also possible to change the anionic sugar liquor obtained into acid form by passing it over a cation exchange resin or by electrodialysis (28).

The syrup of anionic sugars can also be concentrated by evaporation down to 30 to 95% and more particularly 60 to 80% of dry matter (9). The syrup of anionic sugars freed from solid residue has a degree of purity of anionic sugars which is generally between 50 and 95% based on the dry matter.

The third step of the process according to the invention comprises contacting the anionic sugar syrup freed from residue with a $C_{4-22}$-alcohol according to the procedure described for the treatment of raw materials containing no pectins.

For collecting the mixture of alkyl glycosides the process comprises carrying out the same protocol described for the treatment of raw materials containing no pectins.

If the starting substrate contains pectins a second variant of the process comprises, after contacting the fruit, chicory pulp, tubers or Cynara with an aqueous acid solution (FIG. 3 (32)), freeing (33) the sugar syrup from a solid residue (34) in order to obtain a sugar liquor (35), contacting the sugar liquor (35) with chelating salts (36) so as to obtain a liquor of non-charged sugars and sludges (37). In particular, metal cations may be used such as aluminium hydroxide, aluminium sulphate, alkaline earth metal cations such as magnesium, calcium, strontium or barium hydroxides, magnesium, calcium, strontium or barium sulphates, magnesium, calcium, strontium or barium chlorides, optionally converting the liquor of non-charged sugars into acid form by passing over a cation exchange resin or by electrodialysis (39), optionally concentrating the non-charged sugar liquor by evaporation to 30 to 95% and more particularly 60 to 80% of dry matter (310), contacting the non-charged sugar liquor with a $C_{4-22}$-alcohol according to the method described for the treatment of raw materials containing no pectins, collecting the mixture of alkyl glycosides according to the method described for the treatment of raw materials containing no pectins, optionally bringing the sludges (37) into contact with one or more enzymes (311) to obtain hydrolysed sludges, separating the sludges (312) into a liquid and a solid (313), optionally converting the liquid into acid form by passing over a cation exchange resin or by electrodialysis (314), optionally concentrating the liquid by evaporation to 30 to 95% and more particularly 60 to 80% of dry matter (310), bringing the liquid into contact with a $C_{4-22}$-alcohol using the method described for the treatment of raw materials containing no pectins, collecting the mixture of alkyl glycosides according to the method described for the treatment of raw materials containing pectins.

IN PRACTICE:

If the starting substrate contains no pectins (FIG. 1), the process comprises:

mixing the agricultural by-products (1) such as cane trash, maize by-products, sorghum by-products, barley by-products, rice by-products, with an aqueous acid solution. Sulphuric acid, hydrochloric or a sulphosuccinic acid is preferred, homogenising and then cooking the medium at a temperature of between 20 and 150° C., more particularly between 80 and 140° C., for a period of 1 to 90 minutes (2).

The first step may also be carried out by enzymatic hydrolysis. The enzymes used may be a multi-enzyme complex containing hemicellulases, cellulase, β-glucanases, proteases and esterases. The enzymatic hydrolysis is carried out in an aqueous medium for at least one hour at a temperature of between 20 and 90° C.

Pressing the mixture at a pressure of the order of $1.10^5$ to $500.10^5$ Pascals, preferably of the order of $5.10^5$ to $60.10^5$ Pascals by means of a screw press, filter presses, or with any other equipment which can be used to squeeze a liquor from wet residue. This operation (3) makes it possible to isolate a sugar liquor (5) and a residue (4), optionally diluting the residues (4) with at least three times their volume of water and pressing them in a press identical to that used for the first pressing. This operation is not essential but will increase the extraction yield of sugars.

combining the liquors from the presses (sugar liquor 5)

optionally recycling some or all of the crude acid liquor (5) for the hydrolysis of new by-products such as cane trash, maize by-products, barley by-products, rice by-products, preferably with a quantity of crude acid liquor similar to the first dilution. Numerous subsequent recycling processes are possible and can be used to hydrolyse the by-products such as cane trash, maize by-products, barley by-products, rice by-products, without the need for any additional water, with just the quantity of acid being adjusted, optionally precipitating the impurities contained in the sugar liquor in the presence of chelating salts (6). In particular, metal cations may be used such as aluminium hydroxide, aluminium sulphate, alkaline earth metal cations such as magnesium, calcium, strontium or barium hydroxides, magnesium, calcium, strontium or barium sulphates, magnesium, calcium, strontium or barium chlorides.

if necessary, centrifuging the juice obtained by means of equipment used to obtain liquors freed from insoluble matter, such as a horizontal decanter, a filter press, a static decanter, a rotary vacuum filter, tangential filtering systems, a self-cleaning plate centrifuge or a rotary vacuum filter. A juice free from insoluble matter and a centrifuged residue (7) are thus obtained, optionally purifying the sugar solution which is known as the liquor by demineralisation, ion exchange chromatography or low pressure exclusion, by electrodialysis or by a combination of the previous methods (8) whilst preferably leaving at least 0.02 equivalent $H^+$ per mole of sugar, so as to avoid having to add an acid catalyst afterwards. In the chromatography the sugar fraction is therefore combined with some of the salt fraction. In the case of an ion exchange resin, the material is preferably passed successively over a cation exchange resin and an anion exchange resin, the quantity of anion exchange resin possibly being less than at least 0.02 stoichiometric equivalents $H^+$.

optionally converting the sugar liquor by ion exchange on a cation exchange resin or by electrodialysis (9).

if necessary concentrating the sugar syrup by evaporation down to 30 to 95%, more particularly 60 to 80% of dry matter (29, 212). The sugar syrup freed from solid residue has a sugar purity generally between 50 and 95% based on dry matter.

carrying out glycosylation with alcohol, collecting the mixture of surfactant alkyl glycosides.

If the starting substrate contains pectins (FIG. 3), the process comprises:

mixing the agricultural by-products (31) such as the fruits, chicory pulp, tubers and Cynara with an aqueous acid solution. Sulphuric acid, hydrochloric acid or sulphosuccinic acid is preferred, homogenising and then cooking the medium at a temperature of between 20 and 150° C., more particularly between 80 and 140° C., for a period of 1 to 90 minutes (32).

The first step may also be carried out by enzymatic hydrolysis. The enzymes used may be a multi-enzyme complex containing hemicellulases, cellulase, β-glucanases, proteases and esterases and pectinases.

The enzymatic hydrolysis is carried out in an aqueous medium for at least one hour at a temperature of between 20 and 90° C.

Pressing the mixture at a pressure of the order of $1.10^5$ to $500.10^5$ Pascals, preferably of the order of $5.10^5$ to $60.10^5$ Pascals by means of a screw press, filter presses, decanters, or with any other equipment which can be used to squeeze a liquor from wet residue. This operation (33) makes it possible to isolate a sugar liquor (35) and a residue (34), optionally diluting the residues (34) with at least three times their volume of water and pressing them in a press identical to that used for the first pressing. This operation is not essential but will increase the extraction yield of sugars.

combining the liquors from the presses (sugar liquor 35)

optionally recycling some or all of the crude acid liquor (35) for the hydrolysis of new by-products such as fruits, chicory pulp, tubers, Cynara, preferably with a quantity of crude acid liquor similar to the first dilution. Several recycling operations are possible and allow the by-products to be hydrolysed, such as the fruits, chicory pulp, tubers, and Cynara without the need for any additional water, but only adjusting the quantity of acid, optionally purifying the sugar solution which is known as the liquor (35) by demineralisation, ion exchange chromatography or low pressure exclusion, by electrodialysis or by a combination of the previous methods (36) whilst preferably leaving at least 0.02 equivalent $H^+$ per mole of sugar, so as to avoid having to add an acid catalyst afterwards. In the chromatography the sugar fraction is therefore combined with some of the salt fraction. In the case of an ion exchange resin, the material is preferably passed successively over a cation exchange resin and an anion exchange resin, the quantity of anion exchange resin possibly being less than at least 0.02 stoichiometric equivalents $H^+$.

optionally converting the hydrolysate obtained in acid form by passing over a cation exchange resin or by electrodialysis (38), if necessary concentrating the sugar syrup by evaporation down to 30 to 95%, more particularly 60 to 80% of dry matter (39). The sugar syrup freed from solid residue has a sugar purity generally between 50 and 95% based on dry matter.

carrying out glycosylation with alcohol, collecting the mixture of surfactant alkyl glycosides.

If the starting substrate contains pectins according to a first variant (FIG. 2) the process comprises:

mixing the agricultural by-products (21) such as the fruits, chicory pulp, tubers and Cynara with an aqueous acid solution. Sulphuric acid, hydrochloric acid or sulphosuccinic acid is preferred, homogenising and then cooking the medium at a temperature of between 20 and 150° C., more particularly between 80 and 140° C., for a period of 1 to 90 minutes (2).

The first step may also be carried out by enzymatic hydrolysis. The enzymes used may be a multi-enzyme complex containing hemicellulases, cellulase, β-glucanases, proteases and esterases and pectinases. The enzymatic hydrolysis is carried out in an aqueous medium for at least one hour at a temperature of between 20 and 90° C.

Pressing the mixture at a pressure of the order of $1.10^5$ to $500.10^5$ Pascals, preferably of the order of $5.10^5$ to $60.10^5$ Pascals by means of a screw press, filter presses or with any other equipment which can be used to squeeze a liquor from wet residue. This operation (23) makes it possible to isolate a sugar liquor (25) and a residue (24), optionally diluting the residues (24) with at least three times their volume of water and pressing them in a press identical to that used for the first pressing. This operation is not essential but will increase the extraction yield of sugars.

combining the liquors from the presses (sugar liquor 25)

optionally recycling some or all of the crude acid liquor (25) for the hydrolysis of new by-products such as fruits, chicory pulp, tubers, Cynara, preferably with a quantity of crude acid liquor similar to the first dilution. Several recycling operations are possible and allow the by-products to be hydrolysed, such as the fruits, chicory pulp, tubers, and Cynara without the need for any additional water, but only adjusting the quantity of acid, optionally purifying the sugar solution which is known as the liquor (25) by demineralisation, ion exchange chromatography or low pressure exclusion, by electrodialysis or by a combination of the previous methods (26) whilst preferably leaving at least 0.02 equivalent $H^+$ per mole of sugar, so as to avoid having to add an acid catalyst afterwards. In the chromatography the sugar fraction is therefore combined with some of the salt fraction. In the case of an ion exchange resin, the material is preferably passed successively over a cation exchange resin and an anion exchange resin, the quantity of anion exchange resin possibly being less than at least 0.02 stoichiometric equivalents $H^+$.

separating the liquor from enzymatically hydrolysed sugars into a liquor of neutral sugars and a liquor of anionic sugars. This operation (210) can be carried out by electrodialysis or by fixing and then eluting the anionic sugars on an anionic ion exchange resin.

optionally converting the neutral sugar liquor into acid form by passing it over a cation exchange resin or by electrodialysis (28).

if necessary concentrating the neutral sugar syrup by evaporation down to 30 to 95%, more particularly 60 to 80% of dry matter (29). The neutral sugar syrup freed from solid residue has a sugar purity generally between 50 and 95% based on dry matter.

carrying out glycosylation with alcohol, collecting the mixture of surfactant alkyl glycosides.

optionally converting the anionic sugar liquor into acid form by passing over a cation exchange resin or by electrodialysis (211).

if necessary concentrating the anionic sugar syrup by evaporation down to 30 to 95%, more particularly 60 to 80% of dry matter (212). The anionic sugar syrup freed from solid residue has a sugar purity generally between 50 and 95% based on dry matter.

carrying out glycosylation with alcohol, collecting the mixture of surfactant alkyl glycosides.

If the starting substrate contains pectins a according to a second variant (FIG. 3), the process comprises:

mixing the agricultural by-products (31) such as fruits, chicory pulp, tubers or Cynara with an aqueous acid solution. Sulphuric acid, hydrochloric acid or sulphosuccinic acid is preferred, homogenising and then cooking the medium at a temperature of between 20 and 150° C., more particularly between 80 and 140° C., for a period of 1 to 90 minutes (32), pressing the mixture at a pressure of the order of $1.10^5$ to $500.10^5$ Pascals, preferably of the order of $5.10^5$ to $60.10^5$ Pascals by means of a screw press, filter presses or with any other equipment which can be used to squeeze a liquor from wet residue. This operation (33) makes it possible to isolate a sugar liquor (35) and a residue (34), optionally diluting the residues (34) with at least three times their volume of water and pressing them in a press identical to that used for the first pressing. This operation is not essential but will increase the extraction yield of sugars.

combining the liquors from the presses (sugar liquor (35))

optionally recycling some or all of the crude acid liquor (25) for the hydrolysis of new by-products such as fruits, chicory pulp, tubers, Cynara, preferably with a quantity of crude acid liquor similar to the first dilution. Several recycling operations are possible and allow the by-products to be hydrolysed, such as the fruits, chicory pulp, tubers, and Cynara without the need for any additional water, but only adjusting the quantity of acid, contacting the sugar liquors (35) in the presence of chelating salts (36). It is possible in particular to use metal cations such as aluminium hydroxide, aluminium sulphate, alkaline earth metal cations such as magnesium, calcium, strontium or barium hydroxides, magnesium, calcium, strontium or barium sulphates, magnesium, calcium, strontium or barium chlorides.

if necessary centrifuging the liquor obtained using equipment for obtaining liquors freed from insoluble matter, such as a horizontal decanter, a filter press, a static decanter, a rotary vacuum filter, tangential filtering systems, a self-cleaning plate centrifuge or a rotary vacuum filter. The non-charged sugar liquor is then obtained free from insoluble matter and sludges (37). The non-charged sugar liquors consist of pentoses and hexoses and sometimes ketoses, optionally demineralising the non-charged sugar liquor by chromatography on an ion exchange resin or by low pressure exclusion chromatography, by electrodialysis or by a combination of the preceding methods (38).

optionally converting the non-charged sugar liquors by ion exchange on a cation exchange resin or by electrodialysis (39).

if necessary concentrating the non-charged sugar syrup by evaporation down to 30 to 95% and more particularly 60 to 80% of dry matter (310). The non-charged sugar syrup freed from solid residue has a sugar purity generally between 50 and 95% based on dry matter.

carrying out glycosylation of the alcohol with the non-charged sugars, collecting the surfactant alkyl glycosides.

optionally carrying out complementary enzymatic hydrolysis of the sludges (37) in order to obtain enzymatically hydrolysed sludges. This operation comprises contacting the sludges (37) from the operation (36) with pectinases for at least 5 minutes at a temperature of between 10 and 60° C. at a pH of between 3 and 6 (311).

if necessary centrifuging (312) the hydrolysed sludges obtained by means of equipment for obtaining liquors free from insoluble matter, such as a horizontal decanter, a filter press, a static decanter, tangential filtering systems or self-cleaning plate centrifuge. A liquid free from insoluble matter and a solid are thus obtained (313), optionally converting the liquid by ion exchange on a cation exchange resin or by electrodialysis (314).

if necessary concentrating the liquid by evaporation down to 30 to 95% and more particularly 60 to 80% of dry matter (315). The liquid free from solid residue has a purity of anionic sugars generally between 50 and 95% based on dry matter.

carrying out glycosylation of the alcohol with the liquid, collecting the surfactant alkyl glycosides.

The alkyl glycoside mixtures prepared by the process according to the invention have very useful properties and can be used particularly in the fields of detergents, cosmetics and food.

These alkyl glycoside mixtures are remarkable surfactants. In particular, they have solubilising, emulsifying, foaming, wetting and dispersant properties. They can be used as detergents, notably in washing compositions and in compositions for washing dishes, floors and windows, as softeners and as detergent adjuvants in these same compositions, in both powder and liquid form. They may also be included in shampoos or toothpastes and are useful in cosmetics in the form of skin care ointments, creams and lotions for softening and firming the skin, as a gentle surfactant which does not attack either the skin or the mucous membranes. Their foaming and softening powers can also be used to advantage in bath foam preparations. They may also be included in food product formulations as oil and fat additives, in mayonnaise and sauces. In industry, they can be used as agents for polymerisation in dispersions and emulsions. They are also suitable for forming vesicles with liquid crystal properties.

Of these properties, special mention should be made of the property of lowering surface tension particularly of water, as well as the foaming power, the emulsifying power and detergent action.

Of the derivatives prepared by the process according to the invention, those wherein $R^1$ is alkyl, especially $C_{6-14}$-alkyl and preferably $C_{8-12}$-alkyl most preferably $C_{10}$-alkyl are preferred for their good foaming action, which is superior to that of the conventional reference products. The assessment is carried out according to the standard NFT 73404 which consists in pouring 500 ml of surfactant solution into a graduated thermostatically controlled 1000 ml testpiece, at a steady flow rate, containing 50 ml of the same solution. The quantity of foam generated by the pouring is assessed volumetrically just after pouring has ended and then the stability of the volume of foam is evaluated as a function of time over 20 minutes. The mixtures of decyl and dodecyl pentosides have a foaming power superior to that of the surfactants most commonly found, such as sodium dodecyl benzenesulphonate (SDBS), sodium dodecyl sulphate (SDS), sodium lauryl ether sulphate with 2 moles of ethylene oxide (LES) or dodecyl betaine.

With the mixtures prepared by the process according to the invention, the initial volume of foam is 530 ml, whereas it is less than 450 ml for the others. Their foaming power is also greater than that of the alkyl polyglucosides (APG). Moreover, these compounds have very good stability in the foaming time, as the percentage loss is generally less than 5% after 20 minutes.

The mixture of alkyl glycosides prepared by the process according to the invention very effectively lower the surface tension of the water. This property was determined by a conventional method of tensiometry, using a Schlumberger Tensimat no. 3 tensiometer. The measurement is taken at 25° C. The measuring mobile is a rectangular platinum leaf (25 mm×5 mm). When $R^1$ has less than 12 carbon atoms, this reduction in the surface tension of the water is greater than that found with the known products (SDBS, SDS, LES, APG). It is therefore easier to emulsify dirt on laundry.

For their emulsifying power, those compounds wherein $R^1$ is alkyl, especially $C_{8-22}$-alkyl and preferably $C_{14-20}$-alkyl are particularly preferred.

Finally, it should be emphasised that the alkyl glycosides prepared using the process of the invention are entirely biodegradable and harmless to the environment, whilst having good stability.

The compositions produced from the mixtures prepared by the process according to the invention may take different forms, notably powder or liquid detergents, foaming or non-foaming lotions, emulsions of liquid or semi-liquid consistency such as lotions obtained by dispersing an oily phase in an aqueous phase or vice versa, suspensions or emulsions of a soft consistency of the cream or ointment variety or in gel form or solid preparations such as sticks, cleansing bars, impregnated pads or in the form of moisturising masks.

The base for the compositions may be water, organic solvents compatible with topical application, such as acetone, isopropyl alcohol, $C_{6-24}$-fatty acid triglycerides, glycol ethers such as lower alkyl ethers and mono- or dialkylene glycol wherein the alkylene radical has 2 to 4 carbon atoms.

It is also possible to use as the solvent short-chained $C_{1-4}$-polyalkyleneglycol and acid esters, or volatile silicones.

The compositions produced from the mixtures prepared by the process according to the invention may also contain fatty substances such as natural or synthetic oils.

The compositions produced from the mixtures prepared by the process according to the invention may also contain thickeners or gelatinisers such as cellulose or cellulose derivatives. The thickeners may also be acrylic polymers, alginates, gums such as xanthane gum, guar gum, carob gum or gum arabic or polyethylene glycols, bentonites and montmorillonites.

The compositions produced from the mixtures prepared by the process according to the invention may also contain active substances such as hydrating agents as well as adjuvants such as antioxidants, preservatives, perfumes and dyes.

The compositions produced from the mixtures prepared by the process according to the invention may also take the form of solutions or dispersions containing alkyl pentosides in vesicle form, the vesicles possibly acting as encapsulating agents for lipophilic and/or hydrophilic active ingredients.

A powdered detergent composition produced from the mixtures prepared by the process according to the invention contains 0.1 to 60%, preferably 10 to 30% by weight of a detergent base and 99.9 to 40%, preferably 90 to 70% by weight of adjuvants.

The detergent base may be a derivative or a mixture of derivatives prepared by the process according to the invention. It may also be a mixture of one or more derivatives prepared by the process according to the invention with one or more surfactants conventionally used in this field; these surfactants may be anionic, non-ionic, cationic or amphoteric. The proportion of surfactants prepared by the process according to the invention constitutes from 1 to 100% by weight, and preferably 50 to 100% of the total charge of surfactants.

The powdered detergent composition is used in a concentration of 1 to 20 g/l, preferably between 1 and 6 g/l. The washing is done in a conventional machine at between 20 and 80° C., preferably between 20 and 60° C., for a period of 10 to 60 minutes.

A liquid detergent composition produced from derivatives prepared by the process according to the invention contains 0.1 to 60%, preferably 10 to 60% by weight of a detergent base and 99.9 to 40%, preferably 90 to 70% by weight of adjuvants.

The liquid detergent base may be a derivative or a mixture of derivatives prepared by the process. It may also be a mixture of one or more derivatives prepared according to the invention with one or more surfactants conventionally used in this field.

The liquid detergent base produced from derivatives synthesised by the process according to the invention is used in aqueous solution in a concentration of 6 to 12 g/l, at temperatures of from 40 to 70°C.

The Examples which follow illustrate the invention.

EXAMPLE 1

231 g of coarse barley bran containing 95% of dry matter and containing 30% starch, 15% proteins and 30% pentosans relative to the dry matter are brought into contact with 770 g of 3% sulphuric acid solution. The reaction medium is homogenised in a stirred reactor, then heated to a temperature of 130° C. for 30 minutes. After the heat shock, the mixture is brought back to 60° C. and 19 g of flowers of lime containing 90% dry matter are added.

The mixture is then pressed in a MARREL laboratory press to separate the residue 1 from the liquor 1. A liquor and a residue are obtained containing 17% and 55% dry matter, respectively.

The liquor 1 is then demineralised by ion exchange on a strong cationic resin (IRA 200) and a weak anionic resin (IRA 94S). The liquor is then concentrated to 72% dry matter by evaporating the water under reduced pressure; its composition is given in the following Table:

|  | LIQUOR 1 | SYRUP |
| --- | --- | --- |
| dry matter (%) | 17 | 72.0 |
| L-arabinose/dry matter (%) | 7.9 | 10.5 |
| D-xylose/dry matter (%) | 12.3 | 19.3 |
| other sugars/dry matter (%) | 32 | 44 |
| neutral sugars/dry matter (%) | 52.2 | 73.8 |

We obtain 130 g of syrup with a purity of neutral sugars of 73.8%, the pentoses constituting 29.8% of the dry matter.

This syrup is then added dropwise, over 1 hr 30, to 125 g of n-butanol containing 2.8 g of sulphuric acid, at a temperature of the order of 102° C. The water is eliminated during the reaction by azeotropic distillation of the mixture of water and butanol. Then the reaction medium obtained is added to 328 g of fatty alcohol (dodecanol: 70%, tetradecanol: 30%) at a temperature of 90° C. over 2 hours. The butanol is continuously eliminated under reduced pressure during the addition. The acidity of the medium is then neutralised with a 35% aqueous sodium hydroxide solution to pH 7 to 8. The excess fatty alcohols are eliminated by evaporation using a thin layer evaporator and doctor blades under reduced pressure (2 mb) at a temperature of 190° C. The residue (147 g) takes the form of a paste containing less than 3% residual fatty alcohol. This is put into 50% solution in water and decolorised in the presence of oxygenated water.

EXAMPLE 2

260 g of coarse maize bran containing 92% of dry matter and containing 30% starch, 8.5% proteins and 36% pentosans relative to the dry matter are brought into contact with 700 g of 1.8% sulphuric acid solution. The reaction medium is homogenised in a stirred reactor, then heated to a temperature of 140° C. for 30 minutes. After the heat shock, the mixture is pressed in a CARVER laboratory press to separate the residue 1 from the liquor 1. A liquor and a residue are obtained containing 19.5% and 45% dry matter, respectively.

The liquor 1 is then demineralised by ion exchange on a strong cationic resin (IRA 200) and a weak anionic resin (IRA 94S). Its composition is given in the following Table:

|  | LIQUOR 1 | CONCENTRATED SYRUP |
| --- | --- | --- |
| dry matter (%) | 19.5 | 82.5 |
| L-arabinose/dry matter (%) | 15.2 | 9.4 |
| D-xylose/dry matter (%) | 20.2 | 14.2 |
| other sugars/ dry matter (%) | 40 | 59.2 |
| neutral sugars/ dry matter (%) | 75.4 | 82.8 |

This liquor is then concentrated down to a dry matter content of 82.5% by evaporating the water under reduced pressure. We obtain 110 g of syrup with a purity of neutral sugars of 82.8%, the pentoses constituting 23.6% of the dry matter.

This syrup is then added dropwise, over 1 hr 30, to 130 g of n-butanol with 91% dry matter containing 1.7 g of sulphuric acid, at a temperature of the order of 102° C. The water is eliminated during the reaction by azeotropic distillation of the mixture of water and butanol. Then the reaction medium obtained is added to 258 g of fatty alcohol (decanol: 85%, dodecanol: 15%) at a temperature of 90° C. over 2 hours. The butanol is continuously eliminated under reduced pressure during the addition. The acidity of the medium is then neutralised with a 35% aqueous sodium hydroxide solution to pH 7 to 8. The excess fatty alcohols are eliminated by evaporation using a thin layer evaporator and doctor blades under reduced pressure (5 mb) at a temperature of 170° C. The residue (136 g) takes the form of a paste containing less than 3% residual fatty alcohol. This is put into 50% solution in water and decolorised in the presence of oxygenated water.

EXAMPLE 3

110 g of sugar syrup from Example 2 are then added dropwise, over 3 hrs, to 260 g of a fatty alcohol fraction (decanol: 85%, dodecanol: 15%) containing 130 g of dry matter of surfactant from Example 2 and 2.7 g of sulphuric acid, at a temperature of 100° C. The water is eliminated during the reaction by evaporation under reduced pressure. The acidity of the medium is then neutralised with a 35% aqueous sodium hydroxide solution to pH 7 to 8. The excess fatty alcohols are eliminated by evaporation using a thin layer evaporator and doctor blades under reduced pressure (5 mb) at a temperature of 170° C. The residue (127 g) takes the form of a paste containing less than 3% residual fatty alcohol. This is put into 50% solution in water and decolorised in the presence of oxygenated water.

EXAMPLE 4

110 g of sugar syrup from Example 2 are then added dropwise, over 1 hr 30, to 130 g of n-butanol with 91% dry matter containing 2.7 g of sulphuric acid, at a temperature of the order of 102° C. The water is eliminated during the reaction by azeotropic distillation of the mixture of water and butanol. Then the reaction medium obtained is added to 412 g of fatty alcohol (hexadecanol: 50%, octadecanol: 50%) at a temperature of 90° C. over 2 hours. The butanol is continuously eliminated under reduced pressure during the addition. The acidity of the medium is then neutralised with a 35% aqueous sodium hydroxide solution to pH 7 to 8 at a temperature of 60° C. The reaction medium (510 g) is decolorise in the presence of oxygenated water at 60° C. and is then cooled. It takes the form of flakes, consists of 25% surfactant and 70% fatty alcohol and can be used as it is.

EXAMPLE 5

36 g of dried ground cane trash with 96% dry matter containing 5% neutral sugars, 2.5% ash and 18% pentosans, based on dry matter, are brought into contact with 310 g of 0.6% sulphuric acid solution. The reaction mixture is homogenised in a stirred reactor, then heated to a temperature of 120° C. for 30 minutes. After the heat shock, the mixture is pressed in a MARREL laboratory press to separate the residue 1 from the liquor 1. A liquor and a residue are obtained containing 3.93% and 52% dry matter, respectively.

The liquor 1 is then demineralised by ion exchange on a strong cationic resin (IR 120) and a weak anionic resin (IRA 94S). The liquor is then concentrated to 31% dry matter by evaporating the water under reduced pressure; its composition is given in the following Table:

|  | LIQUOR 1 | CONCENTRATED SYRUP |
| --- | --- | --- |
| dry matter (%) | 3.93 | 31 |
| L-arabinose/dry matter (%) | 3.8 | 10 |
| D-xylose/dry matter (%) | 30.43 | 58 |
| other sugars/ dry matter (%) | 3 | 4 |
| neutral sugars/ dry matter (%) | 37.23 | 72 |

This liquor is then concentrated down to a dry matter content of 31% by evaporating the water under reduced pressure. We obtain 17 g of syrup with a purity of neutral sugars of 72%, the pentoses constituting 68% of the dry matter.

This liquor is then added dropwise, over 1 hr, to 7.7 g of n-butanol containing 0.2 g of sulphuric acid, at a temperature of the order of 102° C. The water is eliminated during the reaction by azeotropic distillation of the mixture of water and butanol. Then the reaction medium obtained is added to 17 g of fatty alcohol (decanol: 85%, dodecanol: 15%) at a temperature of 90° C. over 2 hours. The butanol is continuously eliminated under reduced pressure during the addition. The acidity of the medium is then neutralised with a 35% aqueous sodium hydroxide solution to pH 7 to 8. The excess fatty alcohols are eliminated by evaporation using a thin layer evaporator and doctor blades under reduced pressure (5 mb) at a temperature of 170° C. The residue (8.5 g) takes the form of a paste containing less than 2% residual fatty alcohol. This is put into 50% solution in water and decolorised in the presence of oxygenated water.

EXAMPLE 6

500 g of citrus residue containing 31% dry matter and containing 20% pectins, 6.6% proteins and 40% neutral sugars, based on the dry matter, are brought into contact with 449 g of 2.7% sulphuric acid solution. The reaction mixture is homogenised in a stirred reactor, then heated to a temperature of 107° C. for 60 minutes. The mixture is then pressed in a MARREL laboratory press to separate the residue 1 from the liquor 1. A liquor and a residue are obtained containing 10.8% and 35% dry matter, respectively.

The liquor 1 is then brought to 60° C. and 12 g of flowers of lime containing 90% dry matter are added.

The lime-containing liquor is then centrifuged at 4080 g for 5 minutes to separate the liquor 2 from the sediment 1.

A liquor and a sediment are recovered containing 9% and 19% dry matter, respectively.

The liquor is then demineralised by ion exchange on a strong cationic resin (IR 120) and a weak anionic resin (IRA 94S).

The liquor 2 is then permuted over a strong cationic resin and its composition is given in the following Table:

|  | LIQUOR 1 | SYRUP |
|---|---|---|
| dry matter (%) | 10.8 | 81.36 |
| L-arabinose, xylose/dry matter (%) | 17 | 25 |
| glucose, galactose/dry matter (%) | 20 | 45 |
| galacturonic acid/dry matter (%) | 3.5 | 0 |
| total sugars/dry matter (%) | 42.8 | 92.4 |

We obtain 45 g of syrup with a purity of neutral sugars of 92.4%, the pentoses constituting 25% of the dry matter.

This syrup is then added dropwise, over 1 hr 30, to 47 g of n-butanol containing 1.1 g of sulphuric acid, at a temperature of the order of 102° C. The water is eliminated during the reaction by azeotropic distillation of the mixture of water and butanol. Then the reaction medium obtained is added to 104 g of fatty alcohol (decanol: 85%, dodecanol: 15%) at a temperature of 90° C. over 2 hours. The butanol is continuously eliminated under reduced pressure during the addition. The acidity of the medium is then neutralised with a 35% aqueous sodium hydroxide solution to pH 7 to 8. The excess fatty alcohols are eliminated by evaporation using a thin layer evaporator and doctor blades under reduced pressure (5 mb) at a temperature of 160° C. The residue (57 g), which consists of non-ionic surfactants, takes the form of a paste containing less than 2% residual fatty alcohol. This is put into 50% solution in water and decolorised in the presence of oxygenated water.

The sediment is then washed with 40 g of water and centrifuged. A liquor 3 and a residue 2 are obtained.

The residue 2 is rediluted to 50%, then hydrolysed using pectinases (viscozyme L) in a stirred reactor. The temperature of hydrolysis is 45° C., the duration of hydrolysis 12 hours, the pH of the liquor 4.

The mixture is centrifuged at 4080 g for 5 minutes.

A hydrolysate and a residue 3 are obtained containing 8.5% and 25% of dry matter, respectively.

The hydrolysate is then permuted into acid form on a strong cationic resin (Amberlite 200) then concentrated down to 50% dry matter by evaporating the water under reduced pressure; its composition is given in the following Table:

|  | permuted hydrolysate |
|---|---|
| dry matter (%) | 50 |
| galacturonic acid/dry matter (%) | 69 |
| ash/dry matter (%) | 22 |
| sugar purity/dry matter (%) | 75 |

We recover 25 g of syrup having a purity of galacturonic acid of 69%.

This syrup is then added dropwise, over 1 hr. to 15 g of n-butanol containing 0.4 g of sulphuric acid, at a temperature of the order of 102° C. The water is eliminated during the reaction by azeotropic distillation of the mixture of water and butanol. Then the reaction medium obtained is added to 32 g of fatty alcohol (decanol: 85%, dodecanol: 15%) at a temperature of 90° C. over 2 hours. The butanol is continuously eliminated under reduced pressure during the addition. Then a 35% aqueous sodium hydroxide solution is added to neutralise the acid catalyst and saponify the neutral surfactants formed from the galacturonic acid. The final pH is of the order of 7 to 8. The excess fatty alcohols are eliminated by evaporation using a thin layer evaporator and doctor blades under reduced pressure (5 mb) at a temperature of 160° C. The residue (17 g), which consists predominantly of anionic surfactants, takes the form of a paste containing less than 2% residual fatty alcohol. This is put into 50% solution in water and decolorised in the presence of oxygenated water.

EXAMPLE 7

144 g of potato peelings with 27.45% dry matter containing 16% pectins and 27% neutral sugars are brought into contact with 72 g of 5.4% sulphuric acid solution. The reaction mixture is homogenised in a stirred reactor, then heated to a temperature of 107° C. for 60 minutes. The mixture is then pressed in a MARREL laboratory press to separate the residue 1 from the liquor 1.

The liquor 1 is then brought to 60° C. and 12 ml of milk of lime containing 20% dry matter are added.

The lime-containing liquor is then centrifuged at 4080 g for 5 minutes.

A liquor 2 and a sediment are recovered containing 7.6% and 16% dry matter, respectively.

The liquor 2 is then demineralised by ion exchange on a strong cationic resin (IR 120) and a weak anionic resin (IRA 94S).

The demineralised liquor is then permuted over a strong cationic resin and concentrated by evaporation under reduced pressure. The compositions of the liquor 2 and syrup are given in the following Table:

|  | LIQUOR 2 | SYRUP |
|---|---|---|
| dry matter (%) | 7.6 | 75 |
| L-arabinose, xylose/dry matter (%) | 11 | 20 |
| glucose, galactose/dry matter (%) | 22 | 40 |

-continued

|  | LIQUOR 2 | SYRUP |
|---|---|---|
| galacturonic acid/dry matter (%) | 10 | 0 |
| total sugars/dry matter (%) | 49 | 76 |

We obtain 15 g of syrup with a purity of neutral sugars of 78%, the pentoses constituting 20% of the dry matter.

This syrup is then added dropwise, over 1 hr 30, to 15 g of n-butanol containing 0.3 g of sulphuric acid, at a temperature of the order of 102° C. The water is eliminated during the reaction by azeotropic distillation of the mixture of water and butanol. Then the reaction medium obtained is added to 29 g of fatty alcohol (octanol: 50%, decanol: 50%) at a temperature of 90° C. over 2 hours. The butanol is continuously eliminated under reduced pressure during the addition. The acidity of the medium is then neutralised with a 35% aqueous sodium hydroxide solution to pH 7 to 8. The excess fatty alcohols are eliminated by evaporation using a thin layer evaporator and doctor blades under reduced pressure (5 mb) at a temperature of 150° C. The residue (12 g) takes the form of a paste containing less than 2% residual fatty alcohol. This is put into 70% solution in water and decolorised in the presence of oxygenated water.

The sediment is then washed with 100 g of water and centrifuged. A liquor 3 and a residue 2 are obtained.

The residue 2 is rediluted to 50%, then hydrolysed using pectinases (viscozyme L) in a stirred reactor. The temperature of hydrolysis is 45° C., the duration of hydrolysis 12 hours, the pH of the liquor 4.

The mixture is centrifuged at 4080 g for 5 minutes.

A hydrolysate and a residue 3 are obtained containing 6.5% and 23% of dry matter, respectively.

The hydrolysate is then permuted into acid form on a strong cationic resin (Amberlite 200) then concentrated down to 50% dry matter by evaporating the water under reduced pressure; its composition is given in the following Table:

|  | permuted hydrolysate |
|---|---|
| dry matter (%) | 50 |
| galacturonic acid/dry matter (%) | 72 |
| ash/dry matter (%) | 21 |
| sugar purity/dry matter (%) | 76 |

10 g of this syrup are then added dropwise, over 1 hr, to 6 g of n-butanol containing 0.15 g of sulphuric acid, at a temperature of the order of 102° C. The water is eliminated during the reaction by azeotropic distillation of the mixture of water and butanol. Then the reaction medium obtained is added to 12.5 g of decanol at a temperature of 90° C. over 2 hours. The butanol is continuously eliminated under reduced pressure during the addition. Then a 35% aqueous sodium hydroxide solution is added to neutralise the acid catalyst and saponify the neutral surfactants formed from the galacturonic acid. The final pH is of the order of 7 to 8. The excess fatty alcohols are eliminated by evaporation using a thin layer evaporator and doctor blades under reduced pressure (5 mb) at a temperature of 160° C. The residue (7 g), which consists predominantly of anionic surfactants, takes the form of a paste containing less than 2% residual fatty alcohol. This is put into 50% solution in water and decolorised in the presence of oxygenated water.

EXAMPLE 8

10 g of the galacturonic acid syrup of Example 7 are then added dropwise, over 1 hr, to 6 g of n-butanol containing 0.15 g of sulphuric acid, at a temperature of the order of 102° C. The water is eliminated during the reaction by azeotropic distillation of the mixture of water and butanol. Then the reaction medium obtained is added to 12.5 g of decanol at a temperature of 90° C. over 2 hours. The butanol is continuously eliminated under reduced pressure during the addition. Then triethanolamine is added to neutralise the acid catalyst. The final pH is 7. The excess fatty alcohol is eliminated by evaporation using a thin layer evaporator and doctor blades under reduced pressure (5 mb) at a temperature of 150° C. The residue (9 g), which consists predominantly of non-ionic surfactants derived from galacturonic acid, takes the form of a paste containing less than 2% residual fatty alcohol. This is decolorised at 60° C. in the presence of oxygenated water.

EXAMPLE 9

500 g of ground leaves and stems of Cynara 507 with 90% dry matter containing 20% of proteins and 25% of pentosans are brought into contact with 770 g of 0.25% sulphuric acid solution. The reaction mixture is homogenised in a stirred reactor, then heated to a temperature of 120° C. for 60 minutes. The mixture is then pressed in a MARREL laboratory press to separate the residue 1 from the liquor 1. A liquor and a residue are obtained which contain 6.9% and 51.2% dry matter, respectively.

The liquor 1 is then demineralised on a strong cationic resin (Amberlite 200) and a weak anionic resin (A 368S). The liquor is then concentrated to 65% dry matter by evaporating the water under reduced pressure;

|  | LIQUOR 1 | SYRUP |
|---|---|---|
| dry matter (%) | 6.9 | 65.0 |
| L-arabinose/dry matter (%) | 2.6 | 8.2 |
| D-xylose/dry matter (%) | 19.9 | 50.3 |
| other sugars/dry matter (%) | 12.2 | 27.2 |
| total sugars/dry matter (%) | 34.7 | 85.7 |

We obtain 40 g of syrup with a purity of neutral sugars of 85.7%, the pentoses constituting 58.9% of the dry matter.

This syrup is then added dropwise, over 1 hr 30, to 36 g of n-butanol containing 0.8 g of sulphuric acid, at a temperature of the order of 102° C. The water is eliminated during the reaction by azeotropic distillation of the mixture of water and butanol. Then the reaction medium obtained is added to 76.1 g of decanol at a temperature of 90° C. over 2 hours. The butanol is continuously eliminated under reduced pressure during the addition. The acidity of the medium is then neutralised with a 35% aqueous sodium hydroxide solution to pH 7 to 8. The excess fatty alcohols are eliminated by evaporation using a thin layer evaporator and doctor blades under reduced pressure (4 mb) at a temperature of 150° C. The residue (41 g) takes the form of a paste containing less than 2% residual fatty alcohol. This is put into 50% solution in water and decolorised in the presence of oxygenated water.

EXAMPLE 10

1000 g of citrus residue containing 31% dry matter and containing 20% pectins, 6.6% proteins and 40% neutral sugars, based on the dry matter, are brought into contact with 898 g of 2.7% sulphuric acid solution. The reaction mixture is homogenised in a stirred reactor, then heated to a temperature of 107° C. for 60 minutes. The mixture is then pressed in a MARREL laboratory press to separate the residue 1 from the liquor 1. A liquor and a residue are obtained containing 10.8% and 35% dry matter, respectively.

The liquor 1 is then demineralised successively on a strong cationic resin (Amberlite 200) then on an electrodialyser (EUR 2B-20).

The demineralised liquor is then hydrolysed using pectinases (viscozyme L) in a stirred reactor. The temperature of hydrolysis is 45° C., the duration of hydrolysis 12 hours, the pH of the liquor 4.

The composition of the demineralised hydrolysate is given in the following Table:

|  | Hydrolysate | Syrup |
| --- | --- | --- |
| dry matter (%) | 8.8 | 80.2 |
| L-arabinose, xylose/dry matter (%) | 22 | 30 |
| glucose, galactose/dry matter (%) | 20 | 26 |
| galacturonic acid/ dry matter (%) | 14 | 15 |
| total sugars/ dry matter (%) | 66 | 78.5 |

We obtain 120 g of syrup with a purity of neutral sugars of 63.5%, the pentoses constituting 30% of the dry matter.

This syrup is then added dropwise, over 1 hr 30, to 121 g of n-butanol containing 2.9 g of sulphuric acid, at a temperature of the order of 102° C. The water is eliminated during the reaction by azeotropic distillation of the mixture of water and butanol. Then the reaction medium obtained is added to 258 g of decanol at a temperature of 90° C. over 2 hours. The butanol is continuously eliminated under reduced pressure during the addition. Then a 35% aqueous sodium hydroxide solution is added to neutralise the acid catalyst and saponify the neutral surfactants formed from the galacturonic acid. The final pH is of the order of 7 to 8. The excess fatty alcohol is eliminated by evaporation using a thin layer evaporator and doctor blades under reduced pressure (5 mb) at a temperature of 150° C. The residue (142 g), which consists of a mixture of anionic and non-ionic surfactants, takes the form of a paste containing less than 2% residual fatty alcohol. This is put into 50% solution in water and decolorised in the presence of oxygenated water.

EXAMPLE 11

1000 g of citrus residue containing 31% dry matter and containing 20% pectins, 6.6% proteins and 40% neutral sugars, based on the dry matter, are brought into contact with 898 g of 2.7% sulphuric acid solution. The reaction mixture is homogenised in a stirred reactor, then heated to a temperature of 107° C. for 60 minutes. The mixture is then pressed in a MARREL laboratory press to separate the residue 1 from the liquor 1. A liquor and a residue are obtained containing 10.8% and 35% dry matter, respectively.

The liquor 1 is then demineralised successively on a strong cationic resin (Amberlite 200) then on an electrodialyser (EUR 2B-20).

The demineralised liquor is then hydrolysed using pectinases (viscozyme L) in a stirred reactor. The temperature of hydrolysis is 45° C., the duration of hydrolysis 12 hours, the pH of the liquor 4.

The composition of the demineralised hydrolysate is given in the following Table:

|  | Hydrolysate | Syrup |
| --- | --- | --- |
| dry matter (%) | 8.8 | 80.2 |
| L-arabinose, xylose/dry matter (%) | 22 | 25 |
| glucose, galactose/dry matter (%) | 18 | 33 |
| galacturonic acid/ dry matter (%) | 14 | 15 |
| total sugars/ dry matter (%) | 65 | 78.5 |

We obtain 120 g of syrup with a purity of neutral sugars of 63.5%, the pentoses constituting 25% of the dry matter.

This syrup is then added dropwise, over 1 hr 30, to 121 g of n-butanol containing 2.9 g of sulphuric acid, at a temperature of the order of 102° C. The water is eliminated during the reaction by azeotropic distillation of the mixture of water and butanol. Then the reaction medium obtained is added to 258 g of decanol at a temperature of 90° C. over 2 hours. The butanol is continuously eliminated under reduced pressure during the addition. Then triethanolamine is added to neutralise the acid catalyst. The final pH is 7. The excess fatty alcohol is eliminated by evaporation using a thin layer evaporator and doctor blades under reduced pressure (5 mb) at a temperature of 150° C. The residue (151 g), which consists of a mixture of single-chained and double-chained anionic and non-ionic surfactants, takes the form of a paste containing less than 2% residual fatty alcohol. This is decolorised at 60° C. in the presence of oxygenated water.

EXAMPLE 12

885 g of squeezed out, washed orange peel with 22% dry matter containing 20% of pectins, 6.6% proteins and 35% neutral sugars, based on the dry matter, are brought into contact with 895 g of water. The reaction mixture is homogenised in a reactor, then the pH is checked (pH 4). The mixture is heated to a temperature of 50° C. in a stirred reactor and 5 ml of an enzyme cocktail containing essentially pectinases and cellulases are added (viscozyme 120 L) for 12 hours. The mixture is then separated using a laboratory centrifuge at 4080 g for 5 minutes to separate the sludges 1 from the liquor 1. A liquor and sludges are obtained containing 6.8% and 16.35% dry matter, respectively.

The liquor 1 is then permuted into acid form by ion exchange on a strong cationic resin (Amberlite 200).

The liquor 1 is then electrodialysed (electrodialyser of the type EUR 5B-20) and a concentrated liquor and a dilute liquor are obtained, having the following compositions:

| | liquor, dilute compartment | liquor, concentrated compartment |
|---|---|---|
| dry matter (%) | 3.85 | 1.2 |
| L-arabinose/dry matter (%) | 10.45 | 4.6 |
| galactose, fructose/dry matter (%) | 14.6 | 6.7 |
| galacturonic acid/ dry matter (%) | 21.7 | 70 |
| total sugars/ dry matter (%) | 46.75 | 81.3 |

We obtain the concentrated liquor and evaporate it down to obtain 10 g of syrup containing 70% DM. This syrup has an 80% purity of total sugars, galacturonic acid constituting 70% of the dry matter.

This syrup is then added dropwise, over 1 hr 30, to 10.4 g of n-butanol containing 0.25 g of sulphuric acid, at a temperature of the order of 102° C. The water is eliminated during the reaction by azeotropic distillation of the mixture of water and butanol. Then the reaction medium obtained is added to 23 g of fatty alcohol (decanol: 85%, dodecanol: 15%) at a temperature of 90° C. over 2 hours. The butanol is continuously eliminated under reduced pressure during the addition. Then a 35% aqueous sodium hydroxide solution is added to neutralise the acid catalyst and saponify the neutral surfactants formed from the galacturonic acid. The final pH is of the order of 7 to 8. The excess fatty alcohols are eliminated by evaporation using a thin layer evaporator and doctor blades under reduced pressure (5 mb) at a temperature of 160° C. The residue (7 g) which consists primarily of anionic surfactants takes the form of a paste containing less than 2% residual fatty alcohol. This is put into 50% solution in water and decolorised in the presence of oxygenated water.

EXAMPLE 13

Relative reactivities of L-arabinose, D-galacturonic acid and D-glucose

The sugar is suspended in 3 equivalents of decanol in the presence of 3% by mass of sulphuric acid, based on the sugar. The reaction medium is heated to 80° C. and the reaction water is eliminated under reduced pressure (50 mb) as it forms. The progress of the reaction is monitored by GC after silylation of the reaction medium. The results are shown in the following Table.

Comparative Glycosidations of L-arabinose, D-galacturonic Acid and D-glucose

| | RESIDUAL SUGARS (%) | | |
|---|---|---|---|
| time (min) | L-arabinose | D-galacturonic acid | D-glucose |
| 0 | 100 | 100 | 100 |
| 30 | 60 | 0 | 98 |
| 60 | 13 | 0 | 97 |
| 150 | 3.25 | 0 | 42.5 |
| 300 | 2.2 | 0 | 8.5 |
| 390 | | | 0.1 |

Under the reaction conditions defined hereinbefore, it is clear that L-arabinose and D-galacturonic acid react more quickly than D-glucose during glycosylation. After 30 minutes' reaction all the D-galacturonic acid and 40% of the starting L-arabinose have been used up whereas, in the case of glucose, under the same reaction conditions, 98% of residual sugar still remain after 3 minutes.

EXAMPLE 14

Reactivities of D-glucose in the Presence of L-arabinose

The glucose or the mixture of glucose and arabinose are suspended in 3 equivalents of decanol in the presence of 3% by mass of sulphuric acid, based on the sugar. The reaction medium is heated to 80° C. and the water of the reaction is eliminated under reduced pressure (50 mb) as it forms. The progress of the reaction is monitored by GC after silylation of the reaction medium. The results are shown in the following Table.

Comparative Glycosidations of D-glucose on its Own and in the Presence of L-arabinose

| | RESIDUAL SUGARS (%) | | |
|---|---|---|---|
| time (min) | pure D-glucose | D-glucose (+ 90% arabinose) | D-glucose (+ 40% arabinose) |
| 0 | 100 | 100 | 100 |
| 60 | 97 | 40.6 | 63.4 |
| 150 | 42.5 | 14.4 | 19.1 |
| 300 | 8.5 | 11 | 5.75 |
| 530 | 6 | 3.3 | 3.2 |

Under the reaction conditions defined hereinbefore, by using a mixture of D-glucose and L-arabinose as starting material, we have shown that there is a synergy between these two sugars. In fact, D-glucose reacts more quickly in the presence of arabinose than when it is alone in the reaction mixture. After one hour's reaction, when the glucose is on its own in the reaction mixture, 97% of it remains unmodified, whereas when it is treated with, respectively, 90% and 40% of L-arabinose, only 41% and 63% of residual glucose still remain.

What is claimed is:

1. A process for preparing surfactant, comprising contacting a raw material selected from the group consisting of cane trash, products resulting from the processing of maize, products resulting from the processing of sorghum, products resulting from the processing of barley, products resulting from the processing of rice, fruits, products resulting from the production of fruit juice, chicory pulp, tubers, and Cynara for at least 5 seconds with a hydrolysing agent selected from the group consisting of an aqueous acid solution at between 20 and 150° C. and a composition comprising an enzyme capable of hydrolysing plant material at between 20 and 90° C. to obtain a sugar syrup comprising pentoses, freeing the sugar syrup from any solid residues and contacting the residue-free sugar syrup with a $C_{4-22}$-alcohol at a temperature of between 20 and 150° C. until a solution of surfactant glycosides is obtained, and separating the surfactant glycosides from said solution.

2. The process according to claim 1, wherein the sugar syrup is contacted with the $C_{4-22}$-alcohol at a temperature of between 40 and 90° C.

3. The process according to claim 1, wherein the products resulting from the production of fruit juice are selected from the group consisting of citrus pulp, apple residue, and pear residue.

4. The process according to claim 1, wherein the tubers are selected from the group consisting of potatoes and onions.

5. The process according to claim 1, additionally comprising, when the raw material comprises pectins, subjecting the residue-free sugar syrup to enzymatic hydrolysis to form an enzymatically hydrolyzed sugar liquor, wherein the enzymatic hydrolysis is performed before said contacting with an alcohol.

6. The process according to claim 5, further comprising separating said enzymatically hydrolyzed sugar liquor into a neutral sugar liquor comprising neutral sugars and an anionic sugar liquor comprising anionic sugars, and separately bringing the neutral sugar liquor into contact with the $C_{4-22}$-alcohol.

7. The process according to claim 6, wherein the neutral sugars are separated from the anionic sugars by fixing the anionic sugars on ion exchange resins of the anionic type and then recovering said anionic sugars.

8. The process according to claim 1, when the raw material comprises pectins, additionally comprising bringing the residue-free sugar syrup into contact with chelating salts so as to obtain an uncharged sugar liquor and sludges and bringing the uncharged sugar liquor into contact with the $C_{4-22}$-alcohol.

9. The process according to claim 1, wherein the composition comprising an enzyme capable of hydrolysing plant material comprises one or more of the enzymes selected from the group consisting of pectinases, hemicellulases, cellulases, β-glucanases, proteases and esterases.

10. The process according to claim 1, wherein the enzymatic hydrolysis is carried out at a temperature between 20 and 90° C., for at least 5 minutes and at a pH of between 3 and 8.

11. The process according to claim 1, additionally comprising carrying out an operation of permutation into acid form on the residue-free sugar syrup, before bringing said residue-free sugar syrup into contact with an alcohol.

12. The process according to claim 11, wherein the permutation is carried out by bringing the residue-free sugar syrup into contact with a strong cationic resin.

13. The process according to claim 5, additionally comprising contacting the enzymatically hydrolyzed sugar liquor with a saponification agent, wherein said contacting with a saponification agent occurs after said contacting with the $C_{4-22}$-alcohol.

14. The process according to claim 13, wherein sodium hydroxide is used as the saponification agent.

15. The process according to claim 1, wherein the residue-free sugar syrup is contacted with the $C_{4-22}$-alcohol at a temperature of between 30 and 110° C.

16. The process according to claim 6, additionally comprising separately bringing the anionic sugar liquor into contact with $C_{4-22}$-alcohol.

17. The process according to claim 7, wherein the neutral sugars are separated from the anionic sugars by electrodialysis.

18. The process according to claim 8, additionally comprising bringing the sludges into contact with one or more enzymes, in order to obtain hydrolysed sludges, separating said hydrolyzed sludges into a liquid and a solid, and bringing the liquid into contact with a $C_{4-22}$-alcohol.

19. The process according to claim 5, wherein the enzymatic hydrolysis is performed with a composition comprising one or more of the enzymes selected from the group consisting of pectinases, hemicellulases, cellulases, β-glucanases, proteases, and esterases.

20. The process according to claim 18, wherein one or more enzymes are selected from the group consisting of pectinases, hemicellulases, cellulases, β-glucanases, proteases, and esterases.

21. The process according to claim 5, wherein the enzymatic hydrolysis is carried out at a temperature between 20 and 90° C., for at least 5 minutes and at a pH of between 3 and 8.

22. The process according to claims 8, wherein the sludges are brought into contact with enzymes at a temperature between 20 and 90° C., for at least 5 minutes and at a pH of between 3 and 8.

23. The process according to claim 11, wherein the permutation is carried out by electrodialysis.

24. The process according to claim 1, wherein said residue-free sugar syrup is contacted with said $C_{4-22}$ alcohol without further purification of said residue-free sugar syrup beyond freeing the sugar syrup from any solid residues.

25. The process according to claim 1, wherein said sugar syrup comprising pentoses comprises at least 20 weight percent pentose sugars on a dry weight basis.

* * * * *